(12) United States Patent
Khusial et al.

(10) Patent No.: US 8,455,518 B2
(45) Date of Patent: Jun. 4, 2013

(54) METHOD OF TREATING SKIN WITH MICRORNA MODULATORS

(75) Inventors: Permanan Raaj Khusial, Highland Mills, NY (US); Uma Santhanam, Tenafly, NJ (US); John W. Lyga, Basking Ridge, NJ (US)

(73) Assignee: Avon Products, Inc., New York, NY (US)

( * ) Notice: Subject to any disclaimer, the term of this patent is extended or adjusted under 35 U.S.C. 154(b) by 239 days.

(21) Appl. No.: 12/979,695

(22) Filed: Dec. 28, 2010

(65) Prior Publication Data

US 2012/0165373 A1  Jun. 28, 2012

(51) Int. Cl.
*A01N 43/42* (2006.01)
*A61K 31/47* (2006.01)

(52) U.S. Cl.
USPC .......... 514/317; 514/44 A; 514/517; 435/6.13

(58) Field of Classification Search
USPC .............................. 514/331, 44, 517; 434/6.13
See application file for complete search history.

(56) References Cited

U.S. PATENT DOCUMENTS

| | | | |
|---|---|---|---|
| 7,232,806 B2 | 6/2007 | Tuschle et al. | |
| 7,723,030 B2 | 5/2010 | Croce et al. | |
| 2010/0285073 A1 | 11/2010 | Olson et al. | |
| 2011/0263556 A1 | 10/2011 | Priepke et al. | |

FOREIGN PATENT DOCUMENTS

WO  WO 2006133588 A1 * 12/2006
WO  WO 2009018493 A1 *  2/2009

OTHER PUBLICATIONS

PubChem CID 886014. Jul. 9, 2005. {Retrieved from the Internet Mar. 12, 2012: <httpJ/pubchem.ncbi.nlm.nih.gov/summary|summary.cgi?cid=866014&1oc"9C_rcs>].
Gebeshuber, et at miR-29a suppresses tristetraprolin, which is a regulator 01 epithelial polarity and metastasis. EMBO reports 2009, 10:400-405: Abstract.
Ogawa, et al. Suppression of type I collagen production by microRNA-29b in cultured human stellate cells. Biochem!cal and Biophysical Research Communications Jan. 2010, 391 :316-321.
Maurer, et al. MicroRNA-29, a Key Regulator of Collagen Expression in Systemic Sclerosis. Arthritis & Rheumatism Jun. 2010. 62(6):1733-1743.

* cited by examiner

*Primary Examiner* — Brandon Fetterolf
*Assistant Examiner* — Jean Cornet
(74) *Attorney, Agent, or Firm* — Charles J. Zeller; David M. Royal; Joan M. McGillycuddy

(57) ABSTRACT

Methods for preventing, ameliorating, or reducing dermatological signs of aging are provided which employ active agents that suppress or down-regulate microRNA expression in dermal fibroblast, resulting in enhanced production of collagen, elastin and/or fibrillin in the skin. Also provided are methods for screening for activity against specific microRNAs and the methods of using active agents identified by the screening protocol in the treatment of skin.

16 Claims, No Drawings

METHOD OF TREATING SKIN WITH MICRORNA MODULATORS

SEQUENCE LISTING

The instant application contains a Sequence Listing which has been submitted in ASCII format via EFS-Web and is hereby incorporated by reference in its entirety. Said ASCII copy, created on Jan. 3, 2011, is named 38141513.txt and is 553 bytes in size.

FIELD OF INVENTION

The present invention relates generally to methods of improving the aesthetic appearance and health of human skin and also to methods for identifying compounds useful for treating skin. In particular, the invention relates to compounds that reduce levels of certain microRNAs that inhibit expression of collagen, elastin and/or fibrillin in skin cells.

BACKGROUND

Consumers are interested in mitigating or delaying the dermatological signs of aging, such as fine lines, wrinkles, and sagging skin, and related conditions caused by the progressive degradation of the dermal-epidermal junction and of the cell-to-cell cohesion in the epidermis. Chronological aging, hormonal aging, and photo-aging each involve processes that degrade the three main protein components of skin: collagen, elastin, and fibrillin.

Collagen is the body's major structural protein, it supports tissues and organs and connects these structures to bones. Collagen plays a key role in providing the structural scaffolding surrounding cells that helps to support cell shape and differentiation. Elastin is a protein which give skin the ability to stretch and then snap back to its original state. Fibrillin is a glycoprotein, which is essential for the formation of elastic fibers found in connective tissue. Fibrillin is secreted into the extracellular matrix and becomes incorporated into the insoluble microfibrils, which appear to provide a scaffold for deposition of elastin. Collagen, elastin, and fibrillin are produced by fibroblasts, which are specialized skin cells located in the dermis. The stimulation of collagen, elastin, and fibrillin may improve the health and appearance of skin, as skin aging is generally associated with the loss of these proteins. There is a need in the art for compositions that retard skin aging, and which remediate the effects of skin aging.

microRNAs (miRNAs) are short ribonucleic acid (RNA) molecules, on average only about 22 nucleotides long and are found in all eukaryotic cells. miRNAs are believed to be post-transcriptional regulators that bind to complementary sequences on target messenger RNA transcripts (mRNAs), usually resulting in translational repression and gene silencing. If there is complete complementation between the miRNA and target mRNA sequence, the mRNA may be cleaved, leading to direct mRNA degradation. However, if there is not complete complementation, silencing is achieved by preventing translation. It has been estimated that the human genome encodes over 1000 miRNAs, which may target about 60% of mammalian genes and are abundant in many human cell types. However, to date, efforts to improve skin appearance and combat signs of aging, have not focused on the role of microRNAs.

It is therefore an object of the invention to provide compositions and methods for treating, ameliorating, inhibiting and/or preventing dermatological signs of aging.

It is another object of the invention to provide methods for treating, ameliorating, inhibiting and/or preventing dermatological signs of aging by modulating the levels of microRNAs that are related to the expression of collagen, elastin, and/or fibrillin in skin cells.

It is a further object of the invention to provide methods for identifying compounds that are useful for treating, ameliorating, inhibiting and/or preventing dermatological signs of aging, based on the ability to modulate the levels of microRNAs that are related to the expression of collagen, elastin, and/or fibrillin in skin cells.

The foregoing discussion is presented solely to provide a better understanding of nature of the problems confronting the art and should not be construed in any way as an admission as to prior art.

SUMMARY OF THE INVENTION

In accordance with the foregoing objectives and others, it has surprisingly been found that specific microRNAs are negative regulators of collagen, elastin and/or fibrillin expression in skin cells. Methods are therefore provided for improving the aesthetic appearance of human skin comprising topically applying to an area of the skin in need thereof an effective amount of a substance that modulates, preferably by reducing the cellular levels of, microRNA-29a (miR-29a) and/or microRNA-28b (miR-29b), in a cosmetically acceptable vehicle, for a time sufficient to enhance the production of collagen, elastin, and/or fibrillin in the skin. miR-29a comprises the nucleic acid sequence of SEQ. ID. No.: 1 and miR-29b comprises the sequence of SEQ. ID No.: 2, as shown below.

```
                                         (SEQ. ID. No.: 1)
            UAGCACCAUCUGAAAUCGGUUA (SEQ. ID. No.: 2)
            UAGCACCAUUUGAAAUCAGUGUU
```

In various implementations, the method may entail suppressing miR-29a levels in skin cells, suppressing miR-29b levels in skin cells, or suppressing levels of both miR-29a and miR-29b in skin cells. It is contemplated the suppression of both miR-29a and miR-29b in skin cells will provide synergistic benefits in enhancing the expression of collagen, elastin, and/or fibrillin in the skin.

In one aspect, compounds suitable for modulating levels of miR-29a and/or miR-29b may have the structure of formula I:

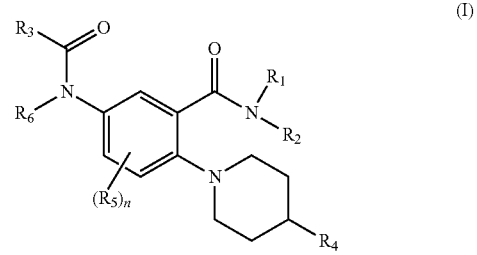

where:

$R_1$ and $R_2$ are independently hydrogen, —R, or —C(=O) R*, wherein $R_1$ and $R_2$ may together with the nitrogen atom to which they are attached form a three to six-membered ring;

$R_3$ is selected from hydrogen, —R, —OR*, —SR*, and —N($R^N$)(R*);

$R^4$ and $R_5$ are independently selected at each occurrence from hydrogen; —R; or $X_1$; and wherein any two adjacent groups $R_5$ may form a five- or six-membered ring fused to the benzene ring to which they are attached;

$R_6$ is hydrogen, —R, or —C(=O)R*;

R, R*, and $R^N$ are independently hydrogen or a $C_{1-20}$ hydrocarbon radical; wherein said $C_{1-20}$ hydrocarbon radical may optionally be substituted with a group $X_1$ and/or with from one to twelve heteroatoms selected from oxygen, nitrogen, and sulfur;

$X_1$ is selected from the group consisting of —F; —Cl; —Br; —I; —OH; —C≡C—R*; —C≡N; —C(R)=N—$R^N$; —C=N—N($R^N$)$_2$; —C(=N$R^N$)—N($R^N$)$_2$; —CH$_2$OH; —CHO; —(C=O)—R*; —CO$_2$H; —CO$_2$; —CO$_2$R*; —CS$_2$R*; —(C=O)—S—R*; —S—(C=O)—R*; —(C=O)—NH$_2$; —(C=O)—N$R^N R^N$; —(C=O)—NHNH$_2$; —O—(C=O)—NHNH$_2$; —(C=S)—NH$_2$; —(C=S)—N($R^N$)$_2$; —O—(C=O)—H; —O—(C=O)—R*; —O—(C=O)—NH$_2$; —O—(C=O)—N$R^N R^N$; —OR*; —SR*: —NH$_2$; —NH$R^N$; —N$R^N_2$; —N($R^N$)$_3^+$; —N($R^N$)—OH; —N(→O)(R*)$_2$; —O—N($R^N$)$_2$; —N($R^N$)—O—R*; —N($R^N$)—N($R^N$)$_2$; —N$R^N$—(C=O)—R*; —N$R^N$C(=O)O—R*; —N$R^N$—CHO; —N$R^N$—(C=O)—R*; —N$R^N$C(=O)N$R^N$; —N($R^N$)—C(=O)—N($R^N$)$_2$; —N($R^N$)—C(=S)—N($R^N$)$_2$; —N=C(R*)$_2$; —N=N—$R^N$; —SCN; —NCS; —NSO; —SS—R*; —SO—R*; —SO$_2$—R*; —O—S(=O)$_2$—R*; —S(=O)$_2$—OR*; —N($R^N$)—SO$_2$—R*; —SO$_2$—N(R*)$_2$; —O—SO$_3^-$; —O—S(=O)$_2$—OR*; —O—S(=O)—OR*; —O—S(=O)—R*; —S(=O)—OR*; —S(=O)—R*; —NO; —NO$_2$; —NO$_3$; —O—NO; —O—NO$_2$; —N$_3$; —N$_2$; —N(C$_2$H$_4$); —Si(R*)$_3$; —CF$_3$; —O—CF$_3$; —(C=O)—R*; —P(R*)$_2$; —O—P(=O)(OR*)$_2$; and —P(=O)(OR*)$_2$;

"n" is an integer from 0 to 3, and, in the case where "n" is 2 or 3, $R_5$ is independently selected at each occurrence;

and cosmetically acceptable acid addition salts thereof.

In some embodiments, $R_1$, $R_2$, $R_3$, $R_4$, and $R_6$, may be independently hydrogen or a group —R, where R is selected from alkyl, alkenyl, alkynyl, aryl, arylalkyl, and alkylaryl, each being optionally substituted with 1-12 heteroatoms selected from halogen, O, N and S. $R_1$ and $R_6$ will usually, but not necessarily, be hydrogen, and $R_2$, $R_3$, and $R_4$ may independently a group —R, where R is a group of the form —(CH$_2$)$_a$—(CR*=CR*)$_b$—(CH$_2$)$_c$—X$_2$—(CH$_2$)$_x$—(CR*=CR*)$_y$—(CH$_2$)$_z$—X$_3$; where a, b, c, x, y, and z are independently integers from 0 to 5, and $X_2$ either represents a bond or a divalent radical or atom selected from —O—, —S—, —C(=O)—, —N($R^N$)—, —C(=O)O—, —OC(=O)—, —C(=O)—N($R^N$)—, —N($R^N$)—C(=O)—, and $X_3$ represents hydrogen, $X_1$, or R*.

In further embodiments, $R_2$ is a group of the form —(CH$_2$)$_a$—X$_2$—(CH$_2$)$_x$—CH$_3$ and/or $R_3$ is a group of the form —CH=CH—R*, wherein R* is an aryl group and/or $R_4$ is a group of the form —(CH$_2$)$_a$—R*, wherein R* is an aryl group. $R_5$ is a substituent at one or more available positions on the benzene ring, but usually hydrogen at all such positions.

In one implementation, the miR-29a and/or miR-29b modulating compound has the formula:

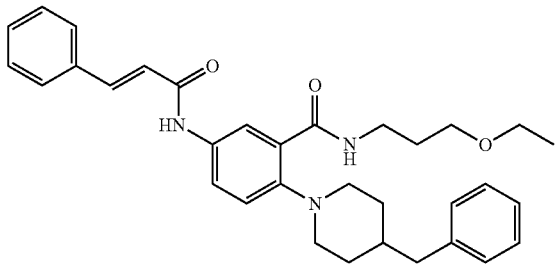 [SMILES: CCOCCCNC(=O)c1cc(NC(=O)/C=C/c2ccccc2)ccc1N1CCC(Cc2ccccc2)CC1]

or a cosmetically acceptable acid addition salt thereof.

Another suitable class of compounds that modulates miR-29a and/or miR-29b has the structure of formula II:

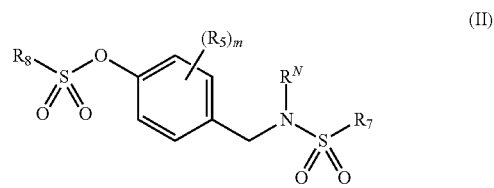

(II)

wherein, $R_5$ is selected from hydrogen; —R; or $X_1$; where "m" is an integer from 0 to 5, and, in the case where "m" is 2, 3 or 4, $R_5$ is independently selected at each occurrence; and $R_7$ and $R_8$ are independently $C_{1-20}$ hydrocarbon radicals; wherein said $C_{1-20}$ hydrocarbon radicals may optionally be substituted with a group $X_1$ and/or with from one to six heteroatoms selected from oxygen, nitrogen, and sulfur; and R, R*, and $R^N$ are independently hydrogen or a $C_{1-20}$ hydrocarbon radical; wherein said $C_{1-20}$ hydrocarbon radical may optionally be substituted with a group $X_1$ (where $X_1$ is defined as above) and/or with from one to twelve heteroatoms selected from oxygen, nitrogen, and sulfur; and cosmetically acceptable salts thereof.

In some variants, $R_7$ and $R_8$ are independently a group —R, where R is a group of the form —(CH$_2$)$_a$—(CR*=CR*)$_b$—(CH$_2$)$_c$—X$_2$—(CH$_2$)$_x$—(CR*=CR*)$_y$—(CH$_2$)$_z$—X$_3$; where a, b, c, x, y, and z are independently integers from 0 to 5, and $X_2$ either represents a bond or a divalent radical or atom selected from —O—, —S—, —C(=O)—, —N($R^N$)—, —C(=O)O—, —OC(=O)—, —C(=O)—N($R^N$)—, —N($R^N$)—C(=O)—, and $X_3$ represents hydrogen, $X_1$, or R*, where R* is a $C_{1-20}$ hydrocarbon radical optionally substituted with a group $X_1$ and/or with from one to twelve heteroatoms selected from oxygen, nitrogen, and sulfur. $R^N$, $R_7$ and $R_8$ may be, for example, independently a group —R, where R is selected from alkyl, alkenyl, alkynyl, aryl, arylalkyl, and alkylaryl, each being optionally substituted with 1-12 heteroatoms selected from halogen, O, N and S. One such useful compound has the formula:

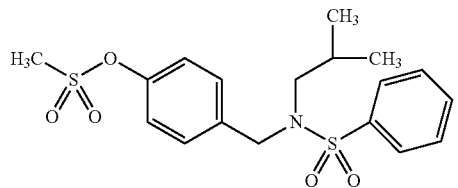 [SMILES: CC(C)CN(Cc1ccc(OS(C)(=O)=O)cc1)S(=O)(=O)c1ccccc1]

In one aspect of the invention, the modulators of miR-29a and/or miR-29b are topically applied to skin in need thereof, for example, wrinkled skin, prematurely thinned skin, or sagging skin, to improve the aesthetic appearance therefore. The improvement may be, for example:

(a) treatment, reduction, and/or prevention of fine lines or wrinkles,
(b) reduction of skin pore size,
(c) improvement in skin thickness, plumpness, and/or tautness;
(d) improvement in skin suppleness and/or softness;
(e) improvement in skin tone, radiance, and/or clarity;
(f) improvement in maintenance and remodeling of elastin;
(g) improvement in skin texture and/or promotion of retexturization;
(h) improvement in skin barrier repair and/or function;
(i) improvement in appearance of skin contours;
(j) restoration of skin luster and/or brightness;
(k) improvement of skin appearance decreased by menopause;
(l) improvement in skin moisturization;
(m) increase in skin elasticity and/or resiliency;
(n) treatment, reduction, and/or prevention of skin sagging; or
(o) reduction of pigment spots.

In another aspect of the invention, a method is provided for identifying active agents useful for improving the aesthetic appearance of skin comprising assaying candidate substances for ability to suppress or down-regulate miR-29a and/or miR-29b in a cell. The assaying step may comprise incubating human dermal fibroblasts with a candidate compound and subsequently measuring the levels of miR-29a and/or miR-29b, for example, by qRT-PCR. Active agents which reduce the levels of miR-29a and/or miR-29b, but preferably both, are expected to be useful in enhancing the levels of collagen, elastin, and/or fibrillin in the skin.

In yet another aspect of the invention, a method is provided for improving the aesthetic appearance of skin by increasing the production of collagen, elastin, and/or fibrillin in the skin, the method comprising topically applying to an area of the skin in need thereof an effective amount of a compound that suppresses miR-29a and/or miR-29b, wherein the compound is identified by an assay which determines the ability of a substance to suppress expression of miR-29a and/or miR-29b in a cell. In one variant, the method is for treating, reducing, or ameliorating wrinkles and fine lines, and comprises topical application of a substance that suppresses miR-29a and miR-29b, wherein the compound is identified by an assay which determines the ability of the substance to suppress levels of miR-29a and/or miR-29b in a cell.

Further aspects, features and advantages of the present invention will be better appreciated upon a reading of the detailed description of the invention.

DETAILED DESCRIPTION OF THE INVENTION

All terms used herein are intended to have their ordinary meaning unless otherwise provided. By "cosmetically acceptable" is meant that a particular component is generally regarding as safe and non-toxic at the levels employed. The term "prevent," as used herein, includes reducing the severity of, or delaying the onset or progression of, a particular sign of skin aging. The term "thin skin" includes skin that becomes thinner with chronological aging as well as prematurely thinned skin, which may be caused, for example, by photoaging. The phrase "individual in need thereof" refers to a human that could benefit from improved dermal appearance or health, including males or females. The term "skin" includes, without limitation, the lips, skin of the face, hands, arms, neck, and chest. As used herein, the term "consisting essentially of" is intended to limit the invention to the specified materials or steps and those that do not materially affect the basic and novel characteristics of the claimed invention, as understood from a reading of this specification.

The present invention provides active agents for preventing, ameliorating, or reducing dermatological signs of aging. The term "active agent" encompasses any substance, including, without limitation, organic molecules; biomolecules (e.g., peptides, proteins, antibodies, nucleic acid oligomers, etc.); and combinations of substances, such as botanical extracts. The active agents modulates the cellular levels of specific microRNAs. Preferably, modulation entails inhibiting, suppressing, or down-regulating microRNAs such that the level of the microRNA is lowered due to the presence of the active agent. The active agents are topically applied to the skin in effective amounts, by which is meant an amount sufficient to achieve a measurable increase in production of collagen, elastin, or fibrillin in the skin.

The active agents are typically applied to the skin for a time sufficient to provide an improvement in one or more dermatological signs of skin aging. Such signs of skin aging include without limitation, the following:

(a) treatment, reduction, and/or prevention of fine lines or wrinkles,
(b) reduction of skin pore size,
(c) improvement in skin thickness, plumpness, and/or tautness;
(d) improvement in skin suppleness and/or softness;
(e) improvement in skin tone, radiance, and/or clarity;
(f) improvement in procollagen and/or collagen production;
(g) improvement in maintenance and remodeling of elastin;
(h) improvement in skin texture and/or promotion of retexturization;
(i) improvement in skin barrier repair and/or function;
(j) improvement in appearance of skin contours;
(k) restoration of skin luster and/or brightness;
(l) replenishment of essential nutrients and/or constituents in the skin;
(m) decreased by aging and/or menopause;
(n) improvement in skin moisturization;
(o) increase in skin elasticity and/or resiliency;
(p) treatment, reduction, and/or prevention of skin sagging and/or
(q) reduction of pigment spots.

In practice, the compositions of the invention are applied to skin in need of treatment. That is, skin which suffers from a deficiency or loss in any of the foregoing attributes or which would otherwise benefit from improvement in any of the foregoing skin attributes. The skin is typically treated once or twice daily. The treatment may continue for a week, two weeks, four weeks, eight weeks, six months or longer.

In one embodiment the active agents are topically applied, in a cosmetically acceptable vehicle, to skin suffering from fine lines and/or wrinkles to prevent, treat, and/or amelioration the appearance of the fine lines and/or wrinkles in the skin. In this case, the compositions are applied to skin in need of treatment, by which is meant skin already having wrinkles and/or fine lines or skin that is at risk of developing fine lines and/or wrinkles. Preferably, the compositions are applied directly to the fine lines and/or wrinkles on the skin of the face, neck, chest, and/or hands.

The invention is premised on the discovery of a novel mechanism of protein regulation in dermal cells involving modulation of cellular microRNAs. The present invention is based on the identification of miR-29a and miR-29b as negative regulators of extracellular matrix proteins, particularly collagen, elastin and fibrillin in skin cells. Experimentation described herein demonstrates that levels of miR-29a and miR-29b increase with age, and that suppression of miR-29a and miR-29b increases production of collagen, eastastin and fibrillin.

The active agents of the instant invention have been shown to reduce levels of miR-29a and miR-29b. *Homo sapiens* miR-29a comprises the nucleic acid sequence of SEQ. ID. No.: 1 and *Homo sapiens* miR-29b comprises the sequence of SEQ. ID No.: 2, as shown below.

```
                                    (SEQ. ID. No.: 1)
UAGCACCAUCUGAAAUCGGUUA (SEQ. ID. No.: 2)
UAGCACCAUUUGAAAUCAGUGUU
```

The active agents may be any substance that reduces the levels of either of these microRNAs. For example, nucleic acid oligomers complementary to the sequence (anti-miRs) may be useful. The anti-miR's are preferably complementary to at least eight consecutive nucleotides of SEQ. ID. No.: 1 or SEQ. ID No.: 2. In other embodiments the anti-miR's are complementary to at least 10, at least 12, at least 14, at least 16, at least 18, or at least 20 consecutive nucleotides of SEQ. ID. No.: 1 or SEQ. ID No.: 2.

The discovery of the correlation between these microRNAs and the production of important skin proteins enables one to screen for active agents that are useful for treating the skin. Accordingly, one embodiment of the invention is a screening method for identifying such active agents. The screening method generally entails contacting skin cells, in particular dermal fibroblasts, with a candidate substance to be tested and culturing the cells for a period of time sufficient to provide a measurable reduction in microRNA levels, which will typically be at least one hour, and more typically from about 12 hours to about 72 hours. The levels of miR-29a and miR-29b are then measured by any technique know in the art for quantitative determination of cellular nucleic acid polymers. A particularly useful method is quantitative RT-PCR (qRT-PCR). By comparing the microRNA levels in the cells treated with the candidate substance to untreated controls, the magnitude of the reduction in microRNA levels can be determined.

Substances that demonstrate the ability to reduce levels of miR-29a and/or miR-29b in human dermal fibroblasts by at least about 5%, preferably at least about 10%, more preferably, at least about 20%, and more preferred still at least about 30%, are selected for use of for further evaluation. In some embodiments, the substances selected are those that reduce levels of miR-29a and/or miR-29b in human dermal fibroblasts by at least about 40%, at least about 50%, or at least about 60%.

In one embodiment, the invention is directed to a method of improving the aesthetic appearance of skin by increasing the production of collagen, elastin, and/or fibrillin in the skin, the method comprising topically applying to an area of the skin in need thereof an effective amount of an active agent that suppresses miR-29a and/or miR-29b, wherein said active agent one that has been identified for use by an assay which determines the ability of a substance to suppress expression of miR-29a and/or miR-29b in a cell, including the assay described herein.

In one embodiment, the active agent comprises a compound capable of modulating levels of miR-29a and/or miR-29b having the structure of formula I:

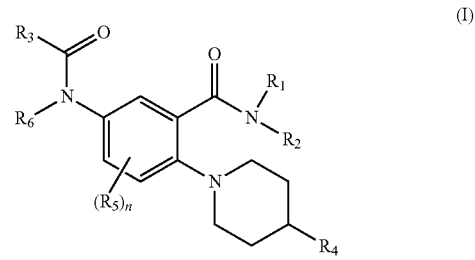

where:

$R_1$ and $R_2$ are independently hydrogen, —R, or —C(=O) R*; and $R_1$ and $R_2$ may together with the nitrogen atom to which they are attached form a three to six-membered ring;

$R^3$ is selected from hydrogen, —R, —OR*, —SR*, and —N($R^N$)(R*);

$R_4$ and $R_5$ are independently selected at each occurrence from hydrogen; —R; or $X_1$; and wherein any two adjacent groups $R_5$ may form a five- or six-membered ring fused to the benzene ring to which they are attached;

$R_6$ is hydrogen, —R, or —C(=O)R*;

R, R*, and $R^N$ are independently hydrogen or a $C_{1-20}$ hydrocarbon radical; or a $C_{1-16}$ hydrocarbon radical, or a $C_{1-12}$ hydrocarbon radical, or a $C_{1-10}$ hydrocarbon radical, wherein said hydrocarbon radical may optionally be substituted with a group $X_1$ and/or with from one to twelve, or from one to eight, or from one to six, or from one to four, heteroatoms selected from oxygen, nitrogen, and sulfur;

$X_1$ is selected from the group consisting of —F; —Cl; —Br; —I; —OH; —C≡C—R*; —C≡N; —C(R)=N—$R^N$; —C=N—N($R^N$)$_2$; —C(=N$R^N$)—N($R^N$)$_2$; —CH$_2$OH; —CHO; —(C=O)—R*; —CO$_2$H; —CO$_2^-$; —CO$_2$R*; —CS$_2$R*; —(C=O)—S—R*; —S—(C=O)—R*; —(C=O)—NH$_2$; —(C=O)—NR$^N$R$^N$; —(C=O)—NHNH$_2$; —O—(C=O)—NHNH$_2$; —(C=S)—NH$_2$; —(C=S)—N($R^N$)$_2$; —O—(C=O)—H; —O—(C=O)—R*; —O—(C=O)—NH$_2$; —O—(C=O)—NR$^N$R$^N$; —OR*; —SR*; —NH$_2$; —NHR$^N$; —NR$^N_2$; —N($R^N$)$_3^+$; —N($R^N$)—OH; —N(→O)(R*)$_2$; —O—N($R^N$)$_2$; —N($R^N$)—O—R*; —N($R^N$)—N($R^N$)$_2$; —NR$^N$—(C=O)—R*; —NR$^N$C(=O)O—R*; —NR$^N$—CHO; —NR$^N$—(C=O)—R*; —NR$^N$C(=O)NR$^N$; —N($R^N$)—C(=O)—N($R^N$)$_2$; —N($R^N$)—C(=S)—N($R^N$)$_2$; —N=C(R*)$_2$; —N=N—R$^N$; —SCN; —NCS; —NSO; —SS—R*; —SO—R*; —SO$_2$—R*; —O—S(=O)$_2$—R*; —S(=O)$_2$—OR*; —N($R^N$)—SO$_2$—R*; —SO$_2$—N(R*)$_2$; —O—SO$_3^-$; —O—S(=O)$_2$—OR*; —O—S(=O)—OR*; —O—S(=O)—R*; —S(=O)—OR*; —S(=O)—R*; —NO; —NO$_2$; —NO$_3$; —O—NO; —O—NO$_2$; —N$_3$; —N$_2$; —N(C$_2$H$_4$); —Si(R*)$_3$; —CF$_3$; —O—CF$_3$; —(C=O)—R*; —P(R*)$_2$; —O—P(=O)(OR*)$_2$; and —P(=O)(OR*)$_2$;

"n" is an integer from 0 to 3 (i.e., 0, 1, 2, or 3), and, in the case where "n" is 2 or 3, $R_5$ is independently selected at each occurrence;

and cosmetically salts thereof, including acid addition salts.

In some embodiments, $R_1$, $R_2$, $R_3$, $R_4$, and/or $R_6$, may be independently hydrogen or a group —R, where R is selected from alkyl, alkenyl, alkynyl, aryl, arylalkyl, and alkylaryl, each being optionally substituted with 1-12 heteroatoms, or from one to eight, or from one to six, or from one to four heteroatoms, selected from halogen, O, N and S, although $R_1$ and $R_2$ are preferably not both hydrogen.

In some embodiments, $R_1$ and/or $R_6$ will be hydrogen, and/or $R_2$, $R_3$, and $R_4$ are independently a group —R, where R has the form —$(CH_2)_a$—$(CR^*$=$CR^*)_b$—$(CH_2)_c$—$X_2$—$(CH_2)_x$—$(CR^*$=$CR^*)_y$—$(CH_2)_z$—$X_3$; where a, b, c, x, y, and z are independently integers from 0 to 5 (i.e., 0, 1, 2, 3, 4, and 5), including the case where a, b, c, x, y, and z are each 0; and $X_2$ either represents a bond or a divalent radical or atom selected from —O—, —S—, —C(=O), —$N(R^N)$—, —C(=O)O—, —OC(=O)—, —C(=O)—$N(R^N)$—, —$N(R^N)$—C(=O)—, and $X_3$ represents hydrogen, $X_1$, or $R^*$.

In further embodiments, $R_2$ is a group of the form —$(CH_2)_a$—$X_2$—$(CH_2)_x$—$CH_3$ and/or $R_3$ is a group of the form —CH=CH—$R^*$, wherein $R^*$ is an aryl group and/or $R_4$ is a group of the form —$(CH_2)_a$—$R^*$, wherein $R^*$ is an aryl group. $R_5$ is a substituent at one or more available positions on the benzene ring, but is usually hydrogen at all such positions.

In one implementation, the miR-29a and/or miR-29b modulating compound is 2-(4-benzylpiperidin-1-yl)-N-(3-ethoxypropyl)-5-[(2E)-3-phenylprop-2enamido]benzamide, having the formula:

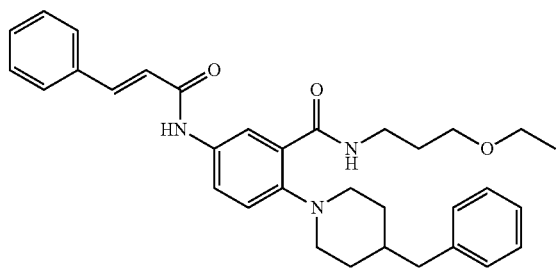 [SMILES: CCOCCCNC(=O)c1cc(NC(=O)/C=C/c2ccccc2)ccc1N1CCC(Cc2ccccc2)CC1]

or a cosmetically acceptable acid addition salt thereof.

In another embodiment, the agent that that modulates miR-29a and/or miR-29b comprises a compound having the structure of formula II:

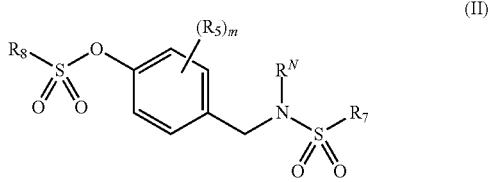

wherein, $R_5$ is selected from hydrogen; —R; or $X_1$; where "m" is an integer from 0 to 5 (i.e., 0, 1, 2, 3, 4, or 5), and, in the case where "m" is 2, 3 or 4, $R_5$ is independently selected at each occurrence; and $R_7$ and $R_8$ are independently $C_{1-20}$ hydrocarbon radicals; or $C_{1-16}$ hydrocarbon radicals, or $C_{1-12}$ hydrocarbon radicals, or $C_{1-10}$ hydrocarbon radicals, wherein said hydrocarbon radicals may optionally be substituted with a group $X_1$ and/or with from one to twelve, or from one to six, or one to four, heteroatoms selected from oxygen, nitrogen, and sulfur; and R, $R^*$, and $R^N$ are independently hydrogen or a $C_{1-20}$ hydrocarbon radical; or a $C_{1-16}$ hydrocarbon radical, or a $C_{1-12}$ hydrocarbon radical, or a $C_{1-10}$ hydrocarbon radical, wherein said hydrocarbon radical may optionally be substituted with a group $X_1$, where $X_1$ is defined as above, and/or with from one to twelve, or from one to six, or from one to four, heteroatoms selected from oxygen, nitrogen, and sulfur; and cosmetically acceptable salts thereof.

In some variants, $R_7$ and $R_8$ are independently a group —R, where R is a group of the form —$(CH_2)_a$—$(CR^*$=$CR^*)_b$—$(CH_2)_c$—$X_2$—$(CH_2)_x$—$(CR^*$=$CR^*)_y$—$(CH_2)_z$—$X_3$; where a, b, c, z, y, and z are independently integers from 0 to 5, and $X_2$ either represents a bond or a divalent radical or atom selected from —O—, —S—, —C(=O)—, —$N(R^N)$—, —C(=O)O—, —OC(=O)—, —C(=O)—$N(R^N)$—, —$N(R^N)$—C(=O)—, and $X_3$ represents hydrogen, $X_1$, or $R^*$, where $R^*$ is a $C_{1-20}$ hydrocarbon radical, or a $C_{1-16}$ hydrocarbon radical, or a $C_{1-12}$ hydrocarbon radical, or a $C_{1-10}$ hydrocarbon radical, or a $C_{1-8}$ hydrocarbon radical, or a $C_{1-6}$ hydrocarbon radical, optionally substituted with a group $X_1$ and/or with from one to twelve heteroatoms, or from one to six heteroatoms, or from one to four heteroatoms, the heteroatoms being selected from oxygen, nitrogen, and sulfur.

$R^N$, $R_7$ and $R_8$ may be, for example, independently a group —R, where R is selected from alkyl, alkenyl, alkynyl, aryl, arylalkyl, and alkylaryl, each being optionally substituted with 1-12 heteroatoms selected from halogen, O, N and S. $R^N$, $R_7$ and $R_8$ may be, for example, independently methyl, ethyl, propyl, isopropyl, butyl, iso-butyl, tert-butyl, pentyl, cyclopentyl, hexyl, cyclohexeyl, phenyl, or benzyl.

One such useful compound is N-(2-methylpropyl)-N-[[4-[(methylsulfonyl)oxy]phenyl]methyl]-benzenesulfonamide which has the structure:

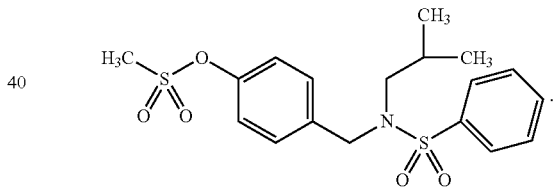

The cosmetic compositions according to the invention can be formulated in a variety of forms for topical application and will comprise from about 0.00001% to about 90% by weight of one or more compounds according to formula (I) or formula (II), and preferably will comprise from about 0.001% to about 25% by weight, and more preferably from about 0.001% to about 1% by weight. The compositions will comprise an effective amount of the compounds of formula (I) or formula (II), by which is meant an amount sufficient to downregulate microRNAs and in turn enhance the production of collagen, elastin and/or fibrillin in a particular area of skin when topically applied thereto.

The compositions can include a cosmetically acceptable vehicle. Such vehicles may take the form of any known in the art suitable for application to skin and may include, but are not limited to, water; vegetable oils; mineral oils; esters such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and biphenyl alcohol; isoparaffins such as isooctane, isododecane and is hexadecane; silicone oils such as cyclomethicone, hydrocarbon oils such as mineral oil, petrolatum, isoeicosane and polyisobutene; polyols such as propylene glycol, glycerin, butylene glycol, pentylene glycol and hexylene glycol; liposomes; waxes; or any combinations or mixtures of the foregoing.

The vehicle may comprise an aqueous phase, an oil phase, an alcohol, a silicone phase or mixtures thereof and may be in the form of an emulsion. Non-limiting examples of suitable emulsions include water-in-oil emulsions, oil-in-water emulsions, silicone-in-water emulsions, water-in-silicone emulsions, glycerin-in-oil emulsions, wax-in-water emulsions, water-oil-water triple emulsions or the like. The emulsion may include an emulsifier, such as a nonionic, anionic or amphoteric surfactant, or a gelling agent.

In one embodiment of the invention, the compositions may include additional skin actives, including but not limited to, botanicals, keratolytic agents, desquamating agents, keratinocyte proliferation enhancers, collagenase inhibitors, elastase inhibitors, depigmenting agents, anti-inflammatory agents, steroids, anti-acne agents, antioxidants, and advanced glycation end-product (AGE) inhibitors.

The composition may comprise additional active ingredients having anti-aging benefits, as it is contemplated that synergistic improvements may be obtained with such combinations. Exemplary anti-aging components include, without limitation, botanicals (e.g., *Butea Frondosa* extract); phytol; thiodipropionic acid (TDPA) and esters thereof; retinoids (e.g., 9-cis retinoic acid, 13-cis retinoic acid, all-trans retinoic acid and derivatives thereof, phytanic acid, retinol (Vitamin A) and esters thereof, such as retinol palmitate, retinol acetate and retinol propionate, and salts thereof and others); hydroxy acids (including alpha-hydroxyacids and beta-hydroxyacids), salicylic acid and alkyl salicylates; exfoliating agents (e.g., glycolic acid, 3,6,9-trioxaundecanedioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); and barrier function enhancing agents (e.g., ceramides, glycerides, cholesterol and its esters, alpha-hydroxy and omega-hydroxy fatty acids and esters thereof, etc.), to name a few. Exemplary retinoids include, without limitation, retinoic acid (e.g., all-trans or 13-cis) and derivatives thereof, retinol (Vitamin A) and esters thereof, such as retinol palmitate, retinol acetate and retinol propionate, and salts thereof.

In another embodiment, the topical compositions of the present invention may also include one or more of the following: a skin penetration enhancer, an emollient, such as isopropyl myristate, petrolatum, silicones (e.g., methicone, dimethicone), oils, mineral oils, and fatty acid esters; a humectant, such as glycerin or caprylyl glycol, a skin plumper, such as palmitoyl oligopeptide, collagen, or collagen and/or glycosaminoglycan (GAG) enhancing agents, a sunscreen, such as avobenzone, an exfoliating agent, and an antioxidant.

Suitable exfoliating agents include, for example, alpha-hydroxyacids, beta-hydroxyacids, oxa-acids, oxadiacids, and their derivatives such as esters, anhydrides and salts thereof. Suitable hydroxy acids include, for example, glycolic acid, lactic acid, malic acid, tartaric acid, citric acid, 2-hydroxyalkanoic acid, mandelic acid, salicylic acid and derivatives thereof. A preferred exfoliating agent is glycolic acid. When present, the exfoliating agent may comprise from about 0.1 wt % to about 80 wt % of the composition.

Examples of antioxidants that may be used in the present compositions include compounds having phenolic hydroxy functions, such as ascorbic acid and its derivatives/esters; beta-carotene; catechins; curcumin; ferulic acid derivatives (e.g. ethyl ferulate, sodium ferulate); gallic acid derivatives (e.g., propyl gallate); lycopene; reductic acid; rosmarinic acid; tannic acid; tetrahydrocurcumin; tocopherol and its derivatives; uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Compositions of the present invention may comprise an antioxidant preferably from about 0.001 wt % to about 10 wt %, and more preferably from about 0.01 wt % to about 5 wt %, of the total weight of the composition.

Other conventional additives include: vitamins, such as tocopherol and ascorbic acid; vitamin derivatives such as ascorbyl monopalmitate; thickeners such as hydroxyalkyl cellulose; gelling agents; structuring agents, metal chelating agents such as EDTA; pigments; colorants, and pH adjusters. The composition may optionally comprise other components known to those skilled in the art including, but not limited to, film formers, moisturizers, minerals, viscosity and/or rheology modifiers, anti-acne agents, insect repellents, skin cooling compounds, skin protectants, lubricants, fragrances, preservatives, stabilizers, and mixtures thereof. In addition to the foregoing, the cosmetic compositions of the invention may contain any other compound for the treatment of skin disorders.

The composition may be formulated in a variety of product forms, such as, for example, an emulsion, lotion, cream, serum, spray, aerosol, cake, ointment, essence, gel, paste, patch, pencil, towelette, mask, stick, foam, elixir, concentrate, and the like, particularly for topical administration. Preferably the composition is formulated as an emulsion, lotion, cream, ointment, serum or gel.

The invention provides a method for treating aging skin by topically applying a composition comprising an active agent that modulated microRNAs that regulate collagen, elastin and/or fibrillin production, including without limitation, a compound of formula I or formula II, preferably in a cosmetically acceptable vehicle, over the affected area for a period of time sufficient to reduce, ameliorate, reverse or prevent dermatological signs of aging.

Generally, the improvement in the condition and/or aesthetic appearance is selected from the group consisting of: reducing dermatological signs of chronological aging, photo-aging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; improving the appearance of suborbital lines and/or periorbital lines; reducing the appearance of crow's feet; rejuvenating and/or revitalizing skin, particularly aging skin; reducing skin fragility; preventing and/or reversing of loss of glycosaminoglycans and/or collagen; ameliorating the effects of estrogen imbalance; preventing skin atrophy; preventing, reducing, and/or treating hyperpigmentation; minimizing skin discoloration; improving skin tone, radiance, clarity and/or tautness; preventing, reducing, and/or ameliorating skin sagging; improving skin firmness, plumpness, suppleness and/or softness; improving procollagen and/or collagen production; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause; improving communication among skin cells; increasing cell proliferation and/or multiplication; increasing skin cell metabolism decreased by aging and/or menopause; retarding cellular aging; improving skin moisturization; enhancing skin thickness; slowing or halting skin thinning; increasing skin elasticity and/or resiliency; enhancing exfoliation; improving microcirculation; decreasing and/or preventing cellulite formation; and any combinations thereof.

The composition will typically be applied to the skin one, two, or three times daily for as long as is necessary to achieve desired results. The treatment regiment may comprise daily application for at least one week, at least two weeks, at least four weeks, at least eight weeks, or at least twelve weeks or more. Chronic treatment regimens are also contemplated. The effect of a composition on the formation or appearance of fine lines and wrinkles can be evaluated qualitatively, e.g., by visual inspection, or quantitatively, e.g., by microscopic or computer assisted measurements of wrinkle morphology (e.g., the number, depth, length, area, volume and/or width of wrinkles per unit area of skin).

It is also contemplated that the compositions of the invention will be useful for treating thin skin by topically applying the composition to thin skin of an individual in need thereof. "Thin skin" is intended to include skin that is thinned due to chronological aging, menopause, or photo-damage and skin that is thinning prematurely. In some embodiments, the treatment is for thin skin in men, whereas other embodiments treat thin skin in women, pre-menopausal or post-menopausal, as it is believed that skin thins differently with age in men and women, and in particular in women at different stages of life.

The method of the invention may be employed prophylactically to forestall aging including in individuals that have not manifested signs of skin aging, most commonly in individuals under 25 years of age. The method may also reverse or treat signs of aging once manifested as is common in individuals over 25 years of age, or to slow the progression of dermatological aging in such individuals.

EXAMPLES

The following examples describe specific aspects of the invention to illustrate the invention but should not be construed as limiting the invention, as the examples merely provide specific methodology useful in the understanding and practice of the invention and its various aspects.

Example 1

Age-Related Expression of miR-29a & miR-29b Levels in Skin Fibroblasts

The expression of miR-29a and miR29b in young versus old skin fibroblasts was examined by qRT-PCR. The experiment was conducted using three sets of donor cells (i.e., three younger donors (age 22-28 yrs) and three older donors (age 55-66 yrs). HDFa cells were grown to about 80% confluence. Cells were lysed using Taqman MicroRNA Cells-to-Ct Kit. cDNA was prepared using miR specific primers and TaqMan MicroRNA Reverse Transcription Kit. qPCR was carried out using predesigned TaqMan MicroRNA Assays for hsa-miR-29a and hsa-miR-29b, and controls RNU6B and GAPDH, purchased from Applied Biosystems. Data summarized in Table 1 below demonstrate that there are significantly higher levels of miR-29a and miR29b in older compared to younger skin fibroblasts.

TABLE 1

| microRNA | Young (%) | Old (%) |
|---|---|---|
| miR-29a | 100 | 350 |
| miR-29b | 100 | 390 |

In Table 1, the data represent an average of 3 donors per age group. All values are statistically significant at $p<0.05$. It is seen that there is a three to four-fold difference in the levels of these microRNAs between these cohorts, with the cells from older donors having sharply increased levels compared to the younger donors.

Example 2

Modulation of ECM Proteins Via Suppression miR-29a and miR-29b

The ability of the specific microRNAs, miR29a and miR29b, to modulate expression of dermal matrix proteins such as collagen, fibrillin and elastin was examined using human dermal fibroblasts from a 55 year-old donor. Cells were transfected with 60 nm of either anti-miR-29a or anti-miR-29b (commercially available reagents) using siSPORT NeoFX transfection Agent (Ambion). Cells were harvested 72 hours post-transfection and the mRNA levels of collagen and fibrillin were determined by qRT-PCR and protein level of elastin was determined by ELISA. These experiments indicated that by suppressing miR-29a or miR-29b, net expression levels of collagen, fibrillin and elastin can be increased (Table 3). All values are statistically significant at $p<0.05$.

TABLE 2

| microRNA | Suppression of miR (%) | Increase in Collagen (%) | Increase in Fibrillin (%) | Increase in Elastin (%) |
|---|---|---|---|---|
| miR-29a | −58 | 130 | 107 | 25 |
| miR-29b | −65 | 140 | 220 | 56 |

As indicated in Table 2, miR-29a and miR-29b were significantly inhibited, 58% and 65%, by their respective anti-miR5. Suppressing miR29a or miR29b in the cells led to an increase in collagen, fibrillin and elastin expression. Collagen 1a, Fibrillin and Elastin were measured as percent change over control without anti-miR.

Example 3

Inhibition of miR-29a or miR-29b by Specific Compounds

Human dermal fibroblasts were grown in the absence of serum overnight, followed by treatment with 0.0005% of test compounds in the absence of serum for 48 hours. Cells were analyzed for expression levels of miR-29a and miR-29b by qRT-PCR as described in Examples 1 and 2. Cells treated with 0.0005% of N-(2-methylpropyl)-N-[[4-[(methylsulfonyl)oxy]phenyl]methyl]-benzenesulfonamide (1) or 2-(4-benzylpiperidin-1-yl)-N-(3-ethoxypropyl)-5-[(2E)-3-phenyl-prop-2-enamido]-benzamide (2) demonstrated a significant inhibition of both miR-29a and miR-29b, relative to vehicle treated cells (Table 3). Cells treated with these compounds also showed increased collagen protein levels as measured by ELISA. All values are statistically significant at $p<0.05$.

TABLE 3

| Compound | Concentration | miR-29a (%) | miR-29b (%) | Collagen (%) |
|---|---|---|---|---|
| 1 | 0.0005% | −61.57 | −85.00 | 102% |
| 2 | 0.0005% | −33.67 | −61.53 | 30% |

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

where:
$R_1$ and $R_2$ are independently hydrogen, —R, or —C(=O)R*, wherein $R_1$ and $R_2$ may together with the nitrogen atom to which they are attached form a three to six-membered ring;
$R_3$ is selected from hydrogen, —R, —OR*, —SR*, and —N($R^N$)(R*);
$R_4$ and $R_5$ are independently selected at each occurrence from hydrogen; —R; or $X_1$; and wherein any two adjacent groups $R_5$ may form a five- or six-membered ring fused to the benzene ring to which they are attached;
$R_6$ is hydrogen, —R, or —C(=O)R*;
R, R*, and $R^N$ are independently hydrogen or a $C_{1-20}$ hydrocarbon radical; wherein said $C_{1-20}$ hydrocarbon radical may optionally be substituted with a group $X_1$ and/or with from one to twelve heteroatoms selected from oxygen, nitrogen, and sulfur;
$X_1$ is selected from the group consisting of —F; —Cl; —Br; —I; —OH; —C≡C—R*; —C≡N; —C(R)=N—$R^N$; —C=N—N($R^N$)$_2$; —C(=N$R^N$)—N($R^N$)$_2$; —CH$_2$OH; —CHO; —(C=O)—R*; —CO$_2$H;

The invention claimed is:
1. A method for improving the aesthetic appearance of human skin comprising topically applying to an area of the skin in need thereof an effective amount of an active agent that suppresses miR-29a, having the sequence UAGCACCAU-CUGAAAUCGGUUA (SEQ. ID. No.: 1), and/or miR-29b, having the sequence UAGCACCAUUUGAAAUCAGU-GUU (SEQ. ID No.: 2), in a cosmetically acceptable vehicle, for a time sufficient to enhance the production of collagen, elastin, and/or fibrillin in the skin, wherein said active agent is a compound having the structure of formula I:

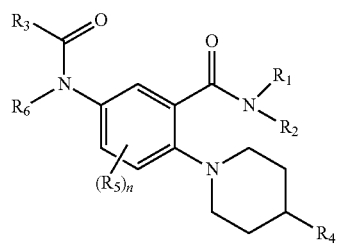

(I)

—CO$_2^-$; —CO$_2$R*; —CS$_2$R*; —(C=O)—S—R*; —S—(C=O)—R*; —(C=O)—NH$_2$; —(C=O)—N$R^N R^N$; —(C=O)—NHNH$_2$; —O—(C=O)—NHNH$_2$; —(C=S)—NH$_2$; —(C=S)—N($R^N$)$_2$; —O—(C=O)—H; —O—(C=O)—R*; —O—(C=O)—NH$_2$; —O—(C=O)—N$R^N R^N$; —OR*; —SR*; —NH$_2$; —NHR$^N$; —NR$^N_2$; —N($R^N$)$_3^+$; —N($R^N$)—OH; —N(→O)(R*)$_2$; —O—N($R^N$)$_2$; —N($R^N$)—O—R*; —N($R^N$)—N($R^N$)$_2$; —NR$^N$—(C=O)—R*; —NR$^N$C(=O)O—R*; —NR$^N$—CHO; —NR$^N$—(C=O)—R*; —NR$^N$C(=O)NR$^N$; —N($R^N$)—C(=O)—N($R^N$)$_2$; —N($R^N$)—C(=S)—N($R^N$)$_2$; —N=C(R*)$_2$; —N=N—R$^N$; —SCN; —NCS; —NSO; —SS—R*; —SO—R*; —SO$_2$—R*; —O—S(=O)$_2$—R*; —S(=O)$_2$OR*; —N($R^N$)—SO$_2$—R*; —SO$_2$—N($R^N$)$_2$; —O—SO$_3^-$; —O—S(=O)$_2$—OR*; —O—S(=O)—OR*; —O—S(=O)—R*; —S(=O)—OR*; —S(=O)—R*; —NO; —NO$_2$; —NO$_3$; —O—NO; —O—NO$_2$; —N$_3$; —N$_2$; —N(C$_2$H$_4$); —Si(R*)$_3$; —CF$_3$; —O—CF$_3$; —(C=O)—R*; —P(R*)$_2$; —O—P(=O)(OR*)$_2$; and —P(=O)(OR*)$_2$;

"n" is an integer from 0 to 3, and, in the case where "n" is 2 or 3, $R_5$ is independently selected at each occurrence; and cosmetically acceptable acid addition salts thereof.

2. The method according to claim 1, wherein said active agent suppresses miR-29a.

3. The method according to claim 1, wherein said active agent suppresses miR-29b.

4. The method according to claim 1, wherein said active agent suppresses miR-29a and miR-29b.

5. The method according to claim 1, wherein $R_1$, $R_2$, $R_3$, $R_4$, and $R_6$, are independently hydrogen or a group —R, where R is selected from alkyl, alkenyl, alkynyl, aryl, arylalkyl, and alkylaryl, each being optionally substituted with 1-12 heteroatoms selected from halogen, O, N and S.

6. The method according to claim 5, wherein $R_2$, $R_3$, and $R_4$ are independently a group —R, where R is a group of the form —$(CH_2)_a$—$(CR^*$=$CR^*)_b$—$(CH_2)_c$—$X_2$—$(CH_2)_x$—$(CR^*$=$CR^*)_y$—$(CH_2)_z$—$X_3$; where a, b, c, x, y, and z are independently integers from 0 to 5, and $X_2$ either represents a bond or a divalent radical or atom selected from —O—, —S—, —C(=O)—, —N($R^N$)—C(=O)O—, —OC(=O)—, —C(=O)—N($R^N$)—, —N($R^N$)—C(=O)—, and $X_3$ represents hydrogen, $X_1$, or R*.

7. The method according to claim 6, wherein $R_1$ and $R_6$ are hydrogen.

8. The method according to claim 7, wherein $R_2$ is a group of the form —$(CH_2)_a$—$X_2$—$(CH_2)_x$—$CH_3$.

9. The method according to claim 7, wherein $R_3$ is a group of the form —CH=CH—R*, wherein R* is an aryl group.

10. The method according to claim 7, wherein $R_4$ is a group of the form —$(CH_2)_a$—R*, wherein R* is an aryl group.

11. The method according to claim 6, wherein $R_5$ is hydrogen.

12. The method according to claim 7, wherein the active agent is a compound having the formula:

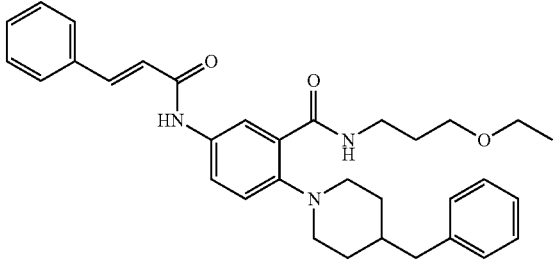 [SMILES: CCOCCCNC(=O)c1cc(NC(=O)/C=C/c2ccccc2)ccc1N1CCC(Cc2ccccc2)CC1]

or a cosmetically acceptable acid addition salt thereof.

13. The method according to claim 1, wherein said aesthetic improvement of said skin is selected from the group consisting of:

(a) treatment, reduction, and/or prevention of fine lines or wrinkles,
(b) reduction of skin pore size,
(c) improvement in skin thickness, plumpness, and/or tautness;
(d) improvement in skin suppleness and/or softness;
(e) improvement in skin tone, radiance, and/or clarity;
(f) improvement in maintenance and remodeling of elastin;
(g) improvement in skin texture and/or promotion of retexturization;
(h) improvement in skin barrier repair and/or function;
(i) improvement in appearance of skin contours;
(j) restoration of skin luster and/or brightness;
(k) improvement of skin appearance decreased by menopause;
(l) improvement in skin moisturization;
(m) increase in skin elasticity and/or resiliency;
(n) treatment, reduction, and/or prevention of skin sagging; or
(o) reduction of pigment spots.

14. A method of improving the aesthetic appearance of skin by increasing the production of collagen, elastin, and/or fibrillin in the skin, said method comprising topically applying to an area of the skin in need thereof an effective amount of an active agent that suppresses miR-29a and/or miR-29b, wherein said active agent is identified by an assay which determines the ability of a substance to suppress expression of miR-29a and/or miR-29b in a cell, wherein said active agent is a compound having the structure of formula I:

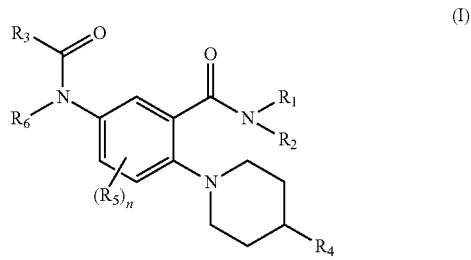

where:
$R_1$ and $R_2$ are independently hydrogen, —R, or —C(=O)R*, wherein $R_1$ and $R_2$ may together with the nitrogen atom to which they are attached form a three to six-membered ring;

$R_3$ is selected from hydrogen, —R, —OR*, —SR*, and —N(RN)(R*);

$R_4$ and $R_5$ are independently selected at each occurrence from hydrogen; —R; or $X_1$; and wherein any two adjacent groups $R_5$ may form a five- or six-membered ring fused to the benzene ring to which they are attached;

$R_6$ is hydrogen, —R, or —C(=O)R*;

R, R*, and $R^N$ are independently hydrogen or a $C_{1-20}$ hydrocarbon radical; wherein said $C_{1-20}$ hydrocarbon radical may optionally be substituted with a group $X_1$ and/or with from one to twelve heteroatoms selected from oxygen, nitrogen, and sulfur;

$X_1$ is selected from the group consisting of —F; —Cl; —Br; —I; —OH; —C≡C—R*; —C≡N; —C(R)=N—$R^N$; —C=N—N($R^N$)$_2$; —C(=N$R^N$)—N($R^N$)$_2$; —$CH_2OH$; —CHO; —(C=O)—R*; —$CO_2H$; —$CO_2^-$; —$CO_2R^*$; —$CS_2R^*$; —(C=O)—S—R*; —S—(C=O)—R*; —(C=O)—$NH_2$; —(C=O)—$NR^N R^N$; —(C=O)—$NHNH_2$; —O—(C=O)—$NHNH_2$; —(C=S)—$NH_2$; —(C=S)—N($R^N$)$_2$; —O—(C=O)—H; —O—(C=O)—R*; —O—(C=O)—$NH_2$; —O—(C=O)—$NR^N R^N$; —OR*; —SR*; —$NH_2$; —$NHR^N$; —$NR^N_2$; —N($R^N$)$_3^+$; —N($R^N$)—OH; —N(→O)($R^*$)$_2$; —O—N($R^N$)$_2$; —N($R^N$)—O—R*; —N($R^N$)—N($R^N$)$_2$; —$NR^N$—(C=O)—R*; —$NR^N$C(=O)O—R*; —$NR^N$—CHO; —$NR^N$—(C=O)—R*; —$NR^N$C(=O)$NR^N$; —N($R^N$)—C(=O)—N($R^N$)$_2$; —N($R^N$)—C(=S)—N($R^N$)$_2$; —N=C($R^*$)$_2$; —N=N—R*; —SCN; —NCS; —NSO; —SS—R*; —SO—R*; —$SO_2$—R*; —O—S(=O)$_2$—R*; —S(=O)$_2$OR*; —N($R^N$)—$SO_2$—R*; —$SO_2$—N($R^*$)$_2$; —O—$SO_3^-$; —O—S(=O)$_2$—OR*;

—O—S(=O)—OR\*; —O—S(=O)—R\*; —S(=O)—OR\*; —S(=O)—R\*; —NO; —NO$_2$; —NO$_3$; —O—NO; —O—NO$_2$; —N$_3$; —N$_2$; —N(C$_2$H$_4$); —Si(R\*)$_3$; —CF$_3$; —O—CF$_3$; —(C=O)—R\*; —P(R\*)$_2$; —O—P(=O)(OR\*)$_2$; and —P(=O)(OR\*)$_2$;

"n" is an integer from 0 to 3, and, in the case where "n" is 2 or 3, R$_5$ is independently selected at each occurrence; and cosmetically acceptable acid addition salts thereof.

15. A method of improving the appearance of aging skin by stimulating extracellular matrix proteins selected from the group consisting of collagen, elastin, fibrillin, and combinations thereof comprising topically applying to the skin in need of such stimulation a composition containing an effective amount of an active agent that suppresses miR-29a and/or miR-29b, in a topically acceptable vehicle, wherein said active agent is a compound having the structure of formula I:

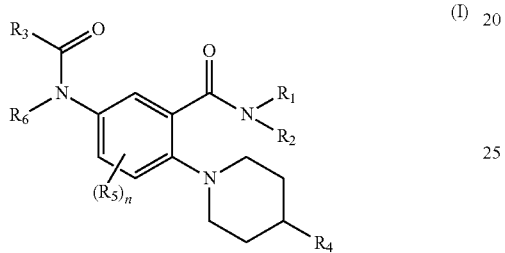

where:
R$_1$ and R$_2$ are independently hydrogen, —R, or —C(=O)R\*, wherein R$_1$ and R$_2$ may together with the nitrogen atom to which they are attached form a three to six-membered ring;
R$_3$ is selected from hydrogen, —R, —OR\*, —SR\*, and —N(RN)(R\*);
R$_4$ and R$_5$ are independently selected at each occurrence from hydrogen; —R; or X$_1$; and wherein any two adjacent groups R$_5$ may form a five- or six-membered ring fused to the benzene ring to which they are attached;
R$_6$ is hydrogen, —R, or —C(=O)R\*;
R, R\*, and R$^N$ are independently hydrogen or a C$_{1-20}$ hydrocarbon radical; wherein said C$_{1-20}$ hydrocarbon radical may optionally be substituted with a group X$_1$ and/or with from one to twelve heteroatoms selected from oxygen, nitrogen, and sulfur;

X$_1$ is selected from the group consisting of —F; —Cl; —Br; —I; —OH; —C≡C—R\*; —C≡N; —C(R)=N—R$^N$; —C=N—N(R$^N$)$_2$; —C(=NR$^N$)—N(R$^N$)$_2$; —CH$_2$OH; —CHO; —(C=O)—R\*; —CO$_2$H; —CO$_2^-$; —CO$_2$R\*; —CS$_2$R\*; —(C=O)—S—R\*; —S—(C=O)—R\*; —(C=O)—NH$_2$; —(C=O)—NR$^N$R$^N$; —(C=O)—NHNH$_2$; —O—(C=O)—NHNH$_2$; —(C=S)—NH$_2$; —(C=S)—N(R$^N$)$_2$; —O—(C=O)—H; —O—(C=O)—R\*; —O—(C=O)—NH$_2$; —O—(C=O)—NR$^N$R$^N$; —OR\*; —SR\*; —NH$_2$; —NHR$^N$; —NR$^N_2$; —N(R$^N$)$_3^+$; —N(R$^N$)—OH; —N(→O)(R\*)$_2$; —O—N(R$^N$)$_2$; —N(R$^N$)—O—R\*; —N(R$^N$)—N(R$^N$)$_2$; —NR$^N$—(C=O)—R\*; —NR$^N$C(=O)O—R\*; —NR$^N$—CHO; —NR$^N$—(C=O)—R\*; —NR$^N$C(=O)NR$^N$; —N(R$^N$)—C(=O)—N(R$^N$)$_2$; —N(R$^N$)—C(=S)—N(R$^N$)$_2$; —N=C(R\*)$_2$; —N=N—R$^N$; —SCN; —NCS; —NSO; —SS—R\*; —SO—R\*; —SO$_2$—R\*; —O—S(=O)$_2$—R\*; —S(=O)$_2$OR\*; —N(R$^N$)—SO$_2$—R\*; —SO$_2$—N(R\*)$_2$; —O—SO$_3^-$; —O—S(=O)$_2$—OR\*; —O—S(=O)—OR\*; —O—S(=O)—R\*; —S(=O)—OR\*; —S(=O)—R\*; —NO; —NO$_2$; —NO$_3$; —O—NO; —O—NO$_2$; —N$_3$; —N$_2$; —N(C$_2$H$_4$); —Si(R\*)$_3$; —CF$_3$; —O—CF$_3$; —(C=O)—R\*; —P(R\*)$_2$; —O—P(=O)(OR\*)$_2$; and —P(=O)(OR\*)$_2$;

"n" is an integer from 0 to 3, and, in the case where "n" is 2 or 3, R$_5$ is independently selected at each occurrence; and cosmetically acceptable acid addition salts thereof.

16. The method according to claim 15, wherein the active agent is a compound having the formula:

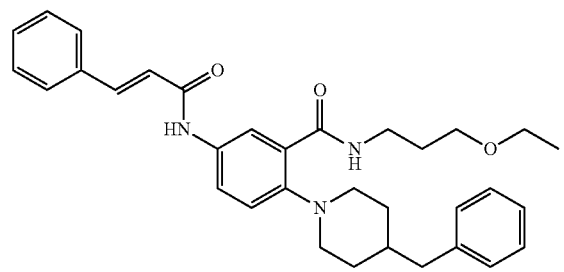 [SMILES: CCOCCCNC(=O)c1cc(NC(=O)/C=C/c2ccccc2)ccc1N1CCC(Cc2ccccc2)CC1]

or a cosmetically acceptable acid addition salt thereof.

* * * * *

SEQUENCE LISTING

<160> NUMBER OF SEQ ID NOS: 2

<210> SEQ ID NO 1
<211> LENGTH: 22
<212> TYPE: RNA
<213> ORGANISM: Homo sapiens

<400> SEQUENCE: 1
uagcaccauc ugaaaucggu ua                                             22

<210> SEQ ID NO 2
<211> LENGTH: 23
<212> TYPE: RNA
<213> ORGANISM: Homo sapiens

<400> SEQUENCE: 2
uagcaccauu ugaaaucagu guu                                            23